US009321730B2

(12) United States Patent
Chan et al.

(10) Patent No.: US 9,321,730 B2
(45) Date of Patent: Apr. 26, 2016

(54) METHOD OF MAKING AND ADMINISTERING QUINOLINE DERIVATIVES AS ANTI-CANCER AGENTS

(75) Inventors: Albert Sun-chi Chan, Hong Kong (CN); Johnny Cheuk-on Tang, Hong Kong (CN); Kim-hung Lam, Hong Kong (CN); Chung-hin Chui, Hong Kong (CN); Stanton Hon-lung Kok, Kowloon (HK); Sau Hing Chan, Hong Kong (CN); Filly Cheung, Hong Kong (CN); Roberto Gambari, Ferrara (IT); Chor Hing Cheng, Hong Kong (CN)

(73) Assignee: The Hong Kong Polytechnic University, Hung Hom, Kowloon (HK)

( * ) Notice: Subject to any disclaimer, the term of this patent is extended or adjusted under 35 U.S.C. 154(b) by 1229 days.

(21) Appl. No.: 11/892,188

(22) Filed: Aug. 21, 2007

(65) Prior Publication Data

US 2009/0054482 A1    Feb. 26, 2009

(51) Int. Cl.
| | | |
|---|---|---|
| *A61K 31/47* | (2006.01) | |
| *C07D 215/06* | (2006.01) | |
| *A61K 31/438* | (2006.01) | |
| *C07D 215/14* | (2006.01) | |
| *C07D 215/18* | (2006.01) | |
| *C07D 215/20* | (2006.01) | |
| *C07D 215/26* | (2006.01) | |
| *A61K 31/4709* | (2006.01) | |

(52) U.S. Cl.
CPC ............ *C07D 215/06* (2013.01); *A61K 31/438* (2013.01); *A61K 31/47* (2013.01); *C07D 215/14* (2013.01); *C07D 215/18* (2013.01); *C07D 215/20* (2013.01); *C07D 215/26* (2013.01); *A61K 31/4709* (2013.01)

(58) Field of Classification Search
CPC .......................... A61K 31/47; A61K 47/4709
See application file for complete search history.

(56) References Cited

U.S. PATENT DOCUMENTS

| 5,405,843 A | 4/1995 | Fukazawa et al. | |
|---|---|---|---|
| 5,541,196 A | 7/1996 | Fournet et al. | |
| 7,619,091 B2 * | 11/2009 | Barnham ................ | A61K 31/47 546/159 |

FOREIGN PATENT DOCUMENTS

| CN | 1219131 | 6/1999 |
|---|---|---|
| CN | 1219131 A | 6/1999 |
| CN | 200880110440.5 | 11/2012 |
| JP | 5-97674 | 4/1993 |
| JP | 5-097674 A | 4/1993 |
| JP | 10-176053 | 6/1998 |
| JP | 5232233 | 3/2013 |
| WO | WO 97/44036 | 5/1997 |
| WO | WO 97/44036 A1 | 11/1997 |
| WO | WO 2006/003405 A1 | 1/2006 |
| WO | WO 2007/147217 | 12/2007 |
| WO | WO 2007147217 A1 | 12/2007 |
| WO | WO 2008/013966 | 1/2008 |
| WO | WO 2008013966 A2 | 1/2008 |
| WO | WO 2009/024095 | 2/2009 |

OTHER PUBLICATIONS

Collet et al. Planta Med., 2002, vol. 68, No. 1, pp. 68-69.*
Abramov, Igor G, et al; "Synthesis of substituted azines with the participation of 4-bromo-5-nitrophthalonitrile"; Mendeleev Commrm., vol. 12, No. 3; (2002) pp. 120-121.
Maffeo, Davide, et al; "Intramolecular sensitisation of europhnn(III) luminescence by 8-benzyloxyquinoline in aqueous solution"; Inorgenika Chimica Acta, 355; (2003); pp. 121-136.
Musiol, Robert, et al; "Antifungal properties of new series of quinoline derivatives"; Bioorganic & Medicinal Chemistry 14 (2006) pp. 3592-3598.
Wang, Wen•Bo, et al; Highly Enantioselective iridium-catalyzed Hydrogenation of Heteroaromatic Compounds, Quinollnes; J. Am. Chem. Soc., vol. 125, (2003); pp. S4-S23.
International Search Report corresponding to International application PCT/CN2008/072092, mailed on Dec. 11, 2011, 4 pages.
Notice of Allowance in JP Pat. Appl. No. 2010-521286 (including English translation), 2010.
Certificate of Patent for JP Patent No. 5232233 (including English translation), 2013.
Office Action issued on Oct. 30, 2012, in JP Pat. Appl. No. 2010-521286 (including English Summary of Office Action).
Decision to Grant European Patent, Application No. 08784083.1, "The Hong Kong Polytechnic University," dated Oct. 10, 2013, 2 pages.
Communication Under Rule 71(3) EPC, Application No. 08784083. 1, "The Hong Kong Polytechnic University," dated Jun. 12, 2013, 45 pages.
Supplemental European Search Report, Application No. 08784083. 1, "The Hong Kong Polytechnic University," dated Jul. 18, 2011.
Wang, W, "Highly Enantioselective Iridium-Catalyzed Hydrogenation of Heteroaromatic Compounds, Quinolines," *J. Am. Chem. Soc.*, vol. 125, No. 35 (2003) pp. 6-30.
Musiol, R., et al., "Antifungal Properties of New Series of Quinoline Derivatives," *Bioorg. Med. Chem. 14*, (2006) pp. 3592-3598.
Maffeo, D., et al., "Intramolecular Sensitisation of Europium(III) Luminescence by 8-benzyloxyquinoline in Aqueous Solution," *J.A. G. Williams Inorganica Chimica Acta 355*, (2003) pp. 127-136.

(Continued)

*Primary Examiner* — Samira Jean-Louis (74) *Attorney, Agent, or Firm* — Duane Morris LLP; Siegfried J. W. Ruppert (57) ABSTRACT

The present invention relates methods of preparing quinoline derivative compounds, and administering such compounds in the treatment of solid and non-solid tumors, notably on liver cancer.

20 Claims, 5 Drawing Sheets

(56) References Cited

OTHER PUBLICATIONS

Abramov, I., et al,, "Synthesis of Substituted Azines with the Participation of 4-bromo-5-nitrophthalonitrile," *Mendeleev Commun.*, (2002) 12(3), pp. 120-121.
Patent Abstracts of Japan corresponds to JP Publication No. 10-176053 dated Jun. 30, 1998.
Statement of Accurate Translation for Chinese Patent No. 200880110440.5, issued Nov. 7, 2012—2 pages.
Statement of Accurate Translation for Japanese Patent No. 5232233, issued Mar. 29, 2013—3 pages.
International Search Report—PCT/CN2008/072092, dated Dec. 11, 2008—4 pages.
Patent Abstract of Japan—Publication No. 05097674A—dated Apr. 20, 1993—1 page.
International Preliminary Report on Patentability—International Appln. No. PCT/CN2008/072092, dated Aug. 21, 2008—9 pages.

* cited by examiner

METHOD OF MAKING AND ADMINISTERING QUINOLINE DERIVATIVES AS ANTI-CANCER AGENTS

BACKGROUND

Many nitrogen-containing basic and biological active compounds isolated from plants, especially those bearing quinoline moiety, offer a broad spectra of biological activities. For instance, quinine and quinidine are widely used for treatment of malaria and cardiac arrhythmias. Luotonin A and B are pyrroloquinazolinoquinoline alkaloids isolated from the aerial parts of Peganum nigellastrum (chinese name "Luo-Tuo-Hao"). This plant is historical used in Chinese traditional medicine for treatment of rheumatism, abscesses and inflammation and are strikingly reminiscent of camptothecin, an inhibitor of topoisomerase I, which are clinically useful anticancer agents. The 8-aminoquinolone, sitamaquine (Walter Reed Army Institute of Research/GlaxoSmit GlaxoSmithKline plc) is an example of quinoline-ring containing alkaloid that is being developed as an alternative oral drug for the treatment of visceral leishmania leishmaniasis. In particular, 8-hydroxyquinoline and its derivatives have been reported for good antifungal properties and can help the treatment of neurodegenerative disease. In addition, the novel quinolium salts and their derivatives have been reported to offer anti-tumor activities with increasing the water solubility.

2-substituted quinoline alkaloids are natural plant products that can be isolated from the root barks, stem barks, and leaves of G. longiflora by fractionation and purification by chromatographic methods. These alkaloids are suggested to be potential anti-leishmanial drugs. 2-substituted tetrahydroquinoline constitute important structural features present in a number of biologically active alkaloids. Angustureine was first isolated by Jacquemond-Collet and his co-workers in 1999 from Galipea officinalis, which has been used in traditional herbal medicine to treat fever of dyspepsia, dysentery and chronic diarrhea. In addition, anti-tuberculous, anti-malarial, and cytotoxic activities have been reported for angustureine. Asymmetric hydrogenation, however, opens a new direction of structural modification to probe its bioactivity. Recent studies demonstrated breakthroughs to the facile production of tetrahydroquinoline derivatives in high enantioselectivities.

The 8-hydroxyquinoline derivatives had been prepared and studied for the treatment of neurodegenerative disease such as Alzheimer's disease. In addition, the derivatives had been reported to possess activities on the proliferation of rat mesenchymal stem cells (rMSCs) and antifungal properties.

It is an objective of the present invention to teach methods of using quinoline derivatives compounds as anti-cancer agents and methods of manufacturing such.

DESCRIPTION

The present invention proposes the preparation of quinoline derivative compounds.

The present invention further proposes administering quinoline derivative compounds in a pharmaceutically acceptable carrier for the treatment of solid and non-solid tumors.

The present invention still further proposes administering quinoline derivative compounds in a pharmaceutically acceptable carrier to solid and non-solid tumors.

These and other features, aspects, and advantages of the apparatus and methods of the present invention will become better understood from the following description, appended claims, and accompanying drawings where:

The following description of certain exemplary embodiment(s) is merely exemplary in nature and is in no way intended to limit the invention, its application, or uses. Throughout this description, the terms "alkyl" and "substituted alkyl" denotes such radicals as straight chain, branched chain or cyclic hydrocarbon groups with 1 to 10 carbon atoms. These alkyl groups are methyl, ethyl, propyl, isopropyl, butyl, isobutyl, sec-butyl, tert-butyl, pentyl, hexyl, heptyl, octyl, nonyl, decyl, cyclopropyl, cyclobutyl, cyclopentyl or cyclohexyl.

The terms "alkenyl" and "substituted alkenyl" denotes such radicals as straight chain, branched chain or cyclic hydrocarbon groups with at least one C=C double bond. These alkenyl groups are vinyl, allyl, propenyl, butenyl, 2-butenyl, 3-butenyl, 1-pentenyl, 2-pentenyl, 3-pentenyl, 4-pentenyl, cyclopentenyl, 1-methyl-cyclopentenyl, 1-hexenyl, 2-hexenyl, 3-hexenyl, 4-hexenyl, 5-hexenyl, cyclohexenyl, 1-heptenyl, 2-heptenyl, 3-heptenyl, 4-heptenyl, 5-heptenyl, 6-heptenyl, 1-octenyl, cyclooctenyl, 1-nonenyl, 2-nonenyl, 3-nonenyl, 1-decenyl, 3-decenyl, 1,3-butadienyl, 1,4-pentadienyl, 1,3-cyclopentadienyl, 1,3-hexadienyl, 1,4-hexadienyl, 1,3-cyclohexadienyl, 1,4-cyclohexadienyl, 1,3-cycloheptadienyl, as well as the straight and branched chain of the trienes.

The terms "acyl" and "substituted acyl" denotes such radicals as aromatic, aliphatic or heterocyclic acyl group, the example the acyl groups are carbamoyl, straight or branch chain alkanoyl, such as, formyl, acetyl, propanoyl, butanoyl, isopropanoyl, pentanoyl, hexnoyl, heptanoyl, octanoyl, nonanoyl, decanoyl, undecanoyl, dodecanoyl, tridecanoyl, tetradecanoyl, pentadecanoyl, hexadecanoyl, heptadecanoyl, octadecanoyl, nonadecanoyl, alkoxycarbonyl, such as, methoxycarbonyl, ethoxycarbonyl, tert-butoxycarbonyl, tert-pentyloxycarbonyl or heptyloxycarbonyl; cycloalkylcarbonyl, such as, cyclopropylcarbonyl, cyclobutylcarbonyl, cyclopentyl, carbonyl or cyclohexylcarbonyl; alkylsulfonyl, such as, methylsulfonyl or ethylsulfonyl; alkoxysulfonyl, such as, methoxysulfonyl or ethoxysulfonyl; aroyl, such as, benxoyl, toluoyl or naphthoyl; aralkanoyl, such as, phenylacetyl, phenylpropanoyl, phenylbutanoyl, phenylisobutyl, phenylpentanoyl, phenylhexanoyl, naphthylacetyl, naphthylpropanoyl, naphthylbutanoyl; aralkenoyl, such as, phenylpropenoyl, phenylpentenoyl, phenylhexenoyl, naphthylpropenoyl, naphthylbutenoyl, naphthylpentenoyl; aralkoxycarbonyl, such as, benzyloxycarbonyl; aryloxycarbonyl, such as, phenoxyacetyl, naphthyloxycarbonyl; aryloxyalkanoyl, such as, phenoxyacetyl, phenoxypropionyl; arycarbamoyl, such as, phenylcarbamoyl, arylthiocarbamoyl, such as, phenylthiocarbamoyl; arylglyoxyloyl, such as, phenylglyoxyloyl, naphthylglyoxyloyl; arylsulfonyl, such as, phenylsulfonyl, naphthylsulfonyl; heterocycliccarbonyl, heterocyclicalkanoyl, such as, thienylacetyl, thienylpropanoyl, thienylbutanoyl, thienylpentanoyl, thienylhexanoyl, thiazolylacetyl, thiadiazolylacetyl or tetrazolylacetyl, heterocyclicalkenoyl, such as, heterocyclicpropenoyl, heterocyclicbutenoyl, heterocyclicpentenoyl or heterocyclichexenoyl, or heterocyclicglyoxyloyl, such as, thiazolylglyoxyloyl or thienyglyoxyloyl.

The terms "aryl" and "substituted aryl" denotes such radicals as carbocyclic aromatic or heterocyclic aromatic system, such as, phenyl, naphthyl, tetrahydronaphthyl, indane or biphenyl. These system may be unsubstituted of substituted by one or more groups, such as, halogen, haloalkyl, hydroxyl, alkoxy, carbonyl, amido, alkylamido, dialkylamido, nitro, amino, alkylamino, dialkylamino, carboxy, thio or thioalkyl.

The terms "heterocyclyl ring" and "substituted heterocyclyl ring" refers to monocyclic or polycyclic heterocyclic groups containing at least one heteroatom, such as, N-containing saturated and unsaturated heterocyclic groups, for example, pyrrolidinyl, imidazolidinyl, piperidino, piperazinyl; pyrrolyl, pyrrolinyl, imidazolyl, pyrazolyl, pyridyl, pyrimidinyl, pyrazinyl, pyridazinyl, triazolyl, tetrazolyl; indolyl, isoindolyl, indolizinyl, benzimidazolyl, quinolyl, isoquinolyl, indazolyl, benzotriazolyl or tetrazolopyridazinyl; O-containing saturated and unsaturated heterocyclic groups, for example, pyranyl, furyl, oxazolyl, isoxazolyl, oxadiazolyl, morpholinyl, benzoxazolyl or benzoxadiazolyl; S-containing saturated and unsaturated heterocyclic groups, for example, thienyl, thiazolyl, thiadiazolyl, thiazolidinyl or thiazolidinyl.

The terms "halo" and "halogen" refer to fluorine, chlorine, bromine or iodine atom which can be one or more halogen atoms.

The terms "hydroxyl" refers to a hydrogen bond to an oxygen atom, the term "substituted hydroxyl" denotes a hydroxyl group substituted with one or more groups, such as, halogen, protected hydroxyl, cyano, nitro, alkyl or substituted alkyl, alkenyl or substituted alkenyl, acyl or substituted acyl, aryl or substituted aryl, heterocyclyl ring or substituted heterocyclyl ring, alkoxy or substituted alkoxy, acyloxy or substituted acyloxy, carboxy or protected carboxy, carboxymethyl or protected carboxymethyl, hydroxymethyl or protected hydroxymethyl, amino or protected amino, carboxamide or protected carboxamide.

The terms "alkoxy" and "substituted alkoxy" refer to straight or branch chain oxo-containing atoms with alkyl, for example, methoxy, ethoxy, propoxy, butoxy, and tetr-butoxy.

The terms "thio" and "substituted thio" refers to radicals containing —SH or —S— group, for examples, methylthio, ethylthio, propylthio, butylthio, hexylthio.

The terms "sulfonyl" and "substituted sulfonyl" refers to radicals containing —S(O)$_2$— group, for examples, methylsulfonyl, ethylsulfonyl, propylsulfonyl, trifluoromethanesulfonyl, trichloromethanesulfonyl or other halogen-substituted alky- or aryl-sulfonyl.

The terms "sulfinyl" and "substituted sulfinyl" refers to radicals containing —S(=O)-group, for examples, methylsulfinyl, ethylsulfinyl, butylsulfinyl, hexylsulfinyl.

Further, as used herein, the term "solid tumor" refers to an abnormal mass of tissue that usually does not contain cysts or liquid areas, including benign and malignant cancers. The term "non-solid tumor" shall refer to hematologic cancers involving the blood-forming cells that naturally migrate to the blood and lymph systems.

The present invention includes methods for preparing quinoline derivative compounds and the use of such quinoline derivative compounds in cancer treatment.

In accordance with the present invention, compounds subject to preparation and use include those represented by formulas I-IV and their salts.

Formulas

I

II

III

IV wherein A, B, C, D and W, X, Y and Z in each formula can be selected individually from the consisting of CH—, CH$_2$—, O, N, P, and S atoms and they may be the specific chiral point(s) (indicated as symbol *) of the compound(s); $R^1$ and $R^2$ in each formula can be selected from the group consisting of H, alkyl, substituted alkyl, alkenyl, substituted alkenyl, alkoxy, substituted alkoxy, hydroxyl, substituted hydroxyl, amino, substituted amino, thio, substituted thio, sulfonyl, substituted sulfonyl, sulfinyl, substituted sulfinyl, sulfonylamino or substituted sulfonylamino, halo, SO$_3$H, amine, CN, CF$_3$, acyl or substituted aryl, heterocyclyl or substituted heterocyclyl, alkoxy or substituted alkoxy, aldehyde or substituted aldehyde or substituted phosphine; COR$^3$, CSR$^3$, and CONHR$^3$ wherein R$^3$ can be selected from the group consisting of H, alkyl, substituted alkyl, alkenyl, substituted alkenyl, hydroxyl, substituted hydroxyl, aryl, substituted aryl, heterocyclyl ring and substituted heterocyclyl ring; OR$^4$, SR$^4$, or NR$^4$R$^5$, wherein, R$^4$ and R$^5$ can independently selected from the group consisting of H, alkyl, substituted alkyl, alkenyl, substituted alkenyl, acyl, substituted acyl, heterocyclyl ring, substituted heterocyclyl ring, and CN; C$_1$ to C$_4$NR$^6$R$^7$, HCNNR$^6$R$^7$, or HCNOR$^6$, wherein R$^6$ and R$^7$ can be alkyl, substituted alkyl, alkenyl, substituted alkenyl, acyl, substituted acyl, heterocyclyl ring, and substituted heterocyclyl ring; SR$^8$, OR$^8$ or NR$^8$R$^9$, where R$^8$ and R$^9$ can be independently selected from the group consisting of H, alkyl, substituted alkyl, alkenyl, substituted alkenyl, acyl, substituted acyl, heterocyclyl ring, and substituted heterocyclyl ring; and SO$_2$NR$^{10}$R$^{11}$ wherein R$^{10}$ and R$^{11}$ can be independently selected from the group consisting of H, alkyl, substituted alkyl, alkenyl, substituted alkenyl, acyl, substituted acyl, heterocyclyl ring, and substituted heterocyclyl ring. $R^1/R^2$ can occur more than once in the ABCD and WXYZ ring moieties, and both $R^1/R^2$ may be specific chiral substituents.

In synthesizing or making the compounds of formulas I-IV, generally, to a solution of a quinoline compound in an ether, a reagent solution, such as n-butyllithium in hexane, is added. The solution is then allowed to warm, preferably to appropriate temperature and stirred for a suitable time, for example 18° C. to 23° C. and stirring for between 0.5 to 3 hours. Further reagents can be added to the solution, for example ketone or alkyl halide (which can contain Br⁻ or I⁻). Additional treatments in producing the desired compounds can include but are not limited to stirring, hydrolysis, hydrogenation, separation, extraction, washing, drying, diluting, and purifying.

Examples of compounds based upon formulas I-IV produced in accordance with the present method include, but are not limited to 2-Ethyl-quinoline

$^1$H-NMR (500 MHz, CDCl$_3$): δ 1.40 (t, 3H, J=8.5 Hz), 3.02 (q, 2H, J=8.0 Hz), 7.31 (d, 1H, J=9.0 Hz), 7.47-7.52 (m, 1H), 7.67-7.70 (m, 1H), 7.78 (d, 1H, J=8.5 Hz), 8.05 (d, 1H, J=8.5 Hz), 8.08 (d, 1H, J=8.0 Hz); $^{13}$C-NMR (125 MHz, CDCl$_3$): δ 14.26, 32.56, 121.08, 125.88, 126.96, 127.71, 129.04, 129.57, 136.58, 148.09, 164.26; Mass spectrum (ESI): 158.09 [M+H]⁺; Yield=90%.

2-Propyl-quinoline

$^1$H-NMR (500 MHz, CDCl$_3$): δ 1.03 (t, 3H, J=7.0 Hz), 1.84-1.88 (m, 2H), 2.96-3.07 (m, 2H), 7.30 (d, 1H, J=8.5 Hz), 7.47-7.49 (m, 1H), 7.61-7.69 (m, 1H), 7.77-7.79 (m, 1H), 8.06 (t, 2H, J=9.0 Hz); $^{13}$C-NMR (125 MHz, CDCl$_3$): δ 14.24, 23.52, 41.51, 121.63, 125.89, 126.96, 127.71, 129.04, 129.57, 136.44, 148.11, 163.14; Mass spectrum (ESI): 172.15 [M+H]⁺; Yield=89%.

2-Butyl-quinoline

$^1$H-NMR (500 MHz, CDCl$_3$): δ 0.97 (t, 3H, J=7.5 Hz), 1.41-1.49 (m, 2H), 1.77-1.83 (m, 2H), 2.98 (t, 2H, J=8.0 Hz), 7.32 (d, 1H, J=8.5 Hz), 7.48 (t, 1H, J=8.0 Hz), 7.67-7.69 (m, 1H), 7.78 (d, 1H, J=8.0 Hz), 8.06 (t, 2H, J=8.5 Hz); $^{13}$C-NMR (125 MHz, CDCl$_3$): δ 14.23, 22.91, 32.44, 39.29, 121.62, 125.90, 126.95, 127.71, 128.98, 129.59, 136.49, 148.05, 163.35; Mass spectrum (ESI): 186.14 [M+H]⁺; Yield=88%.

2-(3-Butenyl)-quinoline

$^1$H-NMR (500 MHz, CDCl$_3$): δ 2.60-2.72 (m, 2H), 3.07-3.09 (m, 2H), 4.95-5.01 (m, 1H), 5.07-5.16 (m, 1H), 5.90-5.96 (m, 1H), 7.30 (d, 1H, J=9.0 Hz), 7.49 (t, 1H, J=7.5 Hz), 7.62-7.69 (m, 1H), 7.77 (d, 1H, J=8.5 Hz), 8.05-8.09 (m, 1H); $^{13}$C-NMR (125 MHz, CDCl$_3$): δ 34.04, 38.71, 115.50, 121.66, 126.02, 127.00, 127.74, 129.01, 129.65, 136.53, 137.91, 148.08, 162.24; Mass spectrum (ESI): 184.11 [M+H]⁺; Yield=92%.

2-Pentyl-quinoline

$^1$H-NMR (500 MHz, CDCl$_3$): δ 0.90 (t, 3H, J=6.0 Hz), 1.35-1.42 (m, 4H), 1.79-1.85 (m, 2H), 2.98 (t, 2H, J=8.0 Hz), 7.30 (d, 1H, J=8.5 Hz), 7.48 (t, 1H, J=8.0 Hz), 7.67-7.70 (m, 1H), 7.77 (d, 1H, J=8.0 Hz), 8.07 (t, 2H, J=8.5 Hz); $^{13}$C-NMR (125 MHz, CDCl$_3$): δ 14.26, 22.81, 30.02, 31.99, 39.53, 121.62, 125.91, 126.95, 127.72, 128.96, 129.61, 136.52, 148.01, 163.36; Mass spectrum (ESI): 200.16 [M+H]⁺; Yield=91%.

2-Phenethyl-quinoline

$^1$H-NMR (500 MHz, CDCl$_3$): δ 3.17 (t, 2H, J=7.0 Hz), 3.30 (t, 2H, J=7.5 Hz), 7.20-7.38 (m, 6H), 7.52 (t, 1H, J=7.5 Hz), 7.71 (t, 1H, J=8.0 Hz), 7.78 (d, 1H, J=8.0 Hz), 8.05 (dd, 2H, J=8.0, 16.0 Hz); $^{13}$C-NMR (125 MHz, CDCl$_3$): δ 36.19, 41.19, 121.82, 126.08, 126.25, 127.05, 127.78, 128.65, 128.77, 129.04, 129.70, 136.55, 141.73, 148.14, 162.04; Mass spectrum (ESI): 234.13 [M+H]⁺; Yield=90%.

2-Methyl-1-(quinolin-2-yl)-propanol

¹H-NMR (500 MHz, CDCl₃): δ 1.20 (s, 6H), 3.04 (s, 2H), 6.09 (s, 1H), 7.19 (d, 1H, J=2.0 Hz), 7.45 (t, 1H, J=8.0 Hz), 7.64 (t, 1H, J=7.5 Hz), 7.73 (d, 1H, J=8.5 Hz), 7.96 (d, 1H, J=8.0 Hz), 8.04 (d, 1H, J=8.5 Hz); ¹³C-NMR (125 MHz, CDCl₃): δ 29.87, 49.26, 71.21, 123.09, 126.42, 126.96, 127.79, 128.96, 130.06, 137.06, 147.09, 161.00. Mass spectrum (ESI): 202.15 [M+H]⁺; Yield=83%.

1,1-Diphenyl-2-(quinolin-2-yl)-ethanol

¹H-NMR (500 MHz, CDCl₃): δ 3.89 (s, 2H), 7.12-7.15 (m, 2H), 7.19-7.26 (m, 4H), 7.46-7.52 (m, 5H), 7.66 (t, 1H, J=8.0 Hz), 7.72 (d, 1H, J=8.5 Hz), 7.97 (d, 1H, J=8.0 Hz), 8.01 (d, 1H, J=8.5 Hz), 8.13 (s, 1H); ¹³C-NMR (125 MHz, CDCl₃): δ 47.77, 78.88, 123.06, 126.42, 126.50, 126.74, 126.83, 127.77, 128.21, 128.74, 130.08, 137.18, 147.54, 160.33; Mass spectrum (ESI): 326.21 [M+H]⁺; Yield=79%.

1-(Quinolin-2-ylmethyl)-cyclohexanol

¹H-NMR (500 MHz, CDCl₃): δ 1.32-1.71 (m, 10H), 3.09 (s, 2H), 7.25 (d, 1H, J=8.5 Hz), 7.48-7.52 (m, 1H), 7.67-7.69 (m, 1H), 7.69-7.71 (m, 1H), 7.78-7.79 (m, 1H), 8.01 (d, 1H, J=8.5 Hz), 8.09 (d, 1H, J=8.0 Hz); ¹³C-NMR (125 MHz, CDCl₃) δ 22.58, 26.16, 38.29, 47.94, 72.17, 123.21, 126.32, 126.92, 127.75, 129.01, 129.95, 136.88, 147.22, 160.80; Mass spectrum (ESI): 242.19 [M+H]⁺; Yield=90%.

Acetic acid quinolin-2-ylmethyl ether

¹H-NMR (500 MHz, CDCl₃): δ 2.20 (s, 3H), 5.40 (s, 2H), 7.48 (d, 1H, J=9.0 Hz), 7.53-7.57 (m, 1H), 7.71-7.74 (m, 1H), 7.83 (d, 1H, J=8.5 Hz), 8.08 (d, 1H, J=8.0 Hz), 8.18 (d, 1H, J=9.0 Hz); ¹³C-NMR (125 MHz, CDCl₃): δ 21.18, 67.68, 119.74, 126.93, 127.77, 127.83, 129.41, 130.09, 137.23, 147.87, 156.37, 170.94; Mass spectrum (ESI): 202.09 [M+H]⁺; Yield=96%.

8-Hydroxy-2-quinolinecarboxaldehyde

¹H-NMR (500 MHz, C₆D₆): δ 6.76-6.79 (m, 1H), 7.05 (d, 1H, J=4.0 Hz), 7.12 (s, 1H), 7.33 (d, 1H, J=9.0 Hz), 7.63 (d, 1H, J=9.0 Hz), 8.02 (s, 1H), 9.79 (s, 1H); ¹³C-NMR (125 MHz, C₆D₆): δ 111.81, 118.33, 118.49, 130.98, 131.35, 137.81, 138.54, 150.99, 154.19, 192.58; Mass spectrum (ESI): 174.05 [M+H]⁺.

8-Methoxy-2-methylquinoline

¹H-NMR (500 MHz, CDCl₃): δ 2.79 (s, 3H), 4.08 (s, 3H), 7.02 (d, 1H, J=8.0 Hz), 7.27-7.41 (m, 3H), 8.01 (d, 1H, J=8.5 Hz); ¹³C-NMR (125 MHz, CDCl₃): δ 25.94, 56.20, 107.81, 119.63, 122.82, 125.90, 127.78, 136.33, 139.90, 155.02, 158.35; Mass spectrum (ESI): 174.09 [M+H]⁺; Yield=84%

8-Ethoxy-2-methylquinoline

¹H-NMR (500 MHz, CDCl₃): δ 1.63 (t, 4H, J=7.0 Hz), 2.80 (s, 3H), 4.34 (q, 2H, J=7.0 Hz), 7.04 (d, 1H, J=7.0 Hz), 7.30-7.40 (m, 3H), 8.01 (d, 1H, J=8.5 Hz); ¹³C-NMR (125 MHz, CDCl₃): δ 14.80, 26.01, 64.54, 108.96, 119.51, 122.70, 125.92, 127.93, 136.33, 140.08, 154.34, 158.33; Mass spectrum (ESI): 188.10 [M+H]⁺

8-(2-(Piperidin-1-yl)ethoxy)-2-methylquinoline

¹H-NMR (500 MHz, CDCl₃): δ 1.46 (bs, 2H), 1.70 (bs, 4H), 2.71 (bs, 7H), 3.04 (bs, 2H), 4.34 (bs, 2H), 6.99 (d, 1H, J=7.0 Hz), 7.24 (d, 1H, J=9.0 Hz), 7.28-7.33 (m, 2H), 7.95 (d, 1H, J=8.5 Hz); ¹³C-NMR (125 MHz, CDCl₃): δ 23.81, 24.88, 25.31, 54.46, 57.31, 64.31, 109.36, 120.26, 122.95, 125.94, 127.98, 136.58, 139.62, 153.83, 158.46; Mass spectrum (ESI): 271.21 [M+H]⁺

8-(Benzyloxy)-2-methylquinoline

¹H-NMR (500 MHz, CDCl₃): δ 2.82 (s, 3H), 5.47 (s, 2H), 7.00 (d, 1H, J=7.5 Hz), 7.27-7.38 (m, 6H), 7.53 (d, 2H, J=8.0 Hz), 7.99 (d, 1H, J=8.5 Hz); ¹³C-NMR (125 MHz, CDCl₃) δ 26.07, 71.06, 110.78, 120.09, 122.76, 125.76, 127.09, 127.85, 128.00, 128.77, 136.28, 137.57, 140.38, 154.12, 158.39; Mass spectrum (ESI): 250.12 [M+H]⁺.

2-Methyl-1,2,3,4-tetrahydroquinoline

¹H-NMR (500 MHz, CDCl₃): δ 1.13 (d, 3H, J=6.5 Hz), 1.47-1.55 (m, 1H), 1.83-1.88 (m, 1H), 2.62-2.79 (m, 3H), 3.29-3.35 (m, 1H), 6.40 (d, 1H, J=8.0 Hz), 6.53 (t, 1H, J=7.0 Hz), 6.87-6.90 (m, 2H); ¹³C-NMR (125 MHz, CDCl₃): δ 22.83, 26.83, 30.36, 47.43, 114.31, 117.29, 121.41, 126.94, 129.53, 144.94; Mass spectrum (ESI): 148.14 [M+H]⁺; 95% ee; HPLC (OJ-H, elute: Hexanes/i-PrOH=95/5, detector: 254 nm, flow rate: 0.5 mL/min), (S) t₁=25.6 min, (R) t₂=28.7 min.

2-Ethyl-1,2,3,4-tetrahydroquinoline

¹H-NMR (500 MHz, CDCl₃): δ 1.02 (t, 3H, J=7.5 Hz), 1.53-1.66 (m, 3H), 1.98-2.03 (m, 1H), 2.74-2.88 (m, 2H), 3.17-3.22 (m, 1H), 6.51 (d, 1H, J=8.0 Hz), 6.63 (t, 1H, J=7.5 Hz), 6.99 (t, 2H, J=7.5 Hz); ¹³C-NMR (125 MHz, CDCl₃) δ 10.32, 26.67, 27.83, 29.65, 53.29, 114.28, 117.15, 121.66, 126.96, 129.49, 144.97; Mass spectrum (ESI): 161.94 [M+H]⁺; 92% ee; HPLC (OJ-H, elute: Hexanes/i-PrOH=95/5, detector: 254 nm, flow rate: 0.5 mL/min), (S) t₁=22.1 min, (R) t₂=24.8 min.

2-Propyl-1,2,3,4-tetrahydroquinoline

¹H-NMR (500 MHz, CDCl₃): δ 0.99 (t, 3H, J=7.5 Hz), 1.42-1.53 (m, 4H), 1.58-1.67 (m, 1H), 1.95-2.00 (m, 1H), 2.72-2.87 (m, 2H), 3.25-3.29 (m, 1H), 6.50 (d, 1H, J=8.0 Hz), 6.62 (t, 1H, J=7.0 Hz), 6.98 (t, 2H, J=7.5 Hz); ¹³C-NMR (125 MHz, CDCl₃): δ 14.45, 19.15, 26.67, 28.35, 39.12, 51.55, 114.31, 117.17, 121.66, 126.94, 129.50, 144.93; Mass spectrum (ESI): 175.94 [M+H]⁺; 88% ee; HPLC (OJ-H, elute: Hexanes/i-PrOH=95/5, detector: 254 nm, flow rate: 0.5 mL/min), (S) t₁=20.3 min, (R) t₂=26.4 min.

2-Butyl-1,2,3,4-tetrahydroquinoline

¹HNMR (500 MHz, CDCl₃): δ 0.97 (t, 3H, J=7.5 Hz), 1.37-1.46 (m, 4H), 1.51-1.53 (m, 2H), 1.60-1.65 (m, 1H), 1.97-2.00 (m, 1H), 2.73-2.89 (m, 2H), 3.27-3.31 (m, 1H), 6.50 (d, 1H, J=7.5 Hz), 6.62 (t, 1H, J=7.5 Hz), 6.98 (t, 2H, J=7.5 Hz); ¹³C-NMR (125 MHz, CDCl₃): δ 14.35, 23.10, 26.68, 28.17, 28.36, 36.66, 51.83, 114.30, 117.15, 121.66, 126.94, 129.50, 144.96; Mass spectrum (ESI): 189.99 [M+H]⁺; 90% ee; HPLC (OJ-H, elute: Hexanes/i-PrOH=95/5, detector: 254 nm, flow rate: 0.5 mL/min), (S) t₁=17.7 min, (R) t₂=21.1 min.

2-Pentyl-1,2,3,4-tetrahydroquinoline

¹H-NMR (500 MHz, CDCl₃): δ 0.83 (t, 3H, J=6.5 Hz), 1.18-1.43 (m, 9H), 1.48-1.56 (m, 1H), 1.86-1.91 (m, 1H), 2.62-2.77 (m, 2H), 3.13-3.18 (m, 1H), 6.40 (d, 1H, J=8.0 Hz), 6.52 (t, 1H, J=7.5 Hz), 6.88 (t, 2H, J=7.0 Hz); ¹³C-NMR (125 MHz, CDCl₃): δ 14.32, 22.91, 25.65, 26.69, 28.36, 32.22, 36.92, 51.85, 114.30, 117.15, 121.66, 126.94, 129.50, 144.96; Mass spectrum (ESI): 204.01 [M+H]⁺; 91% ee;

HPLC (OJ-H, elute: Hexanes/i-PrOH=95/5, detector: 254 nm, flow rate: 0.5 mL/min), (S) t₁=15.7 min, (R) t₂=17.3 min.

2,6-Dimethyl-1,2,3,4-tetrahydroquinoline

¹H-NMR (500 MHz, CDCl₃): δ 1.22 (d, 3H, J=6.5 Hz), 1.56-1.64 (m, 1H), 1.91-1.96 (m, 1H), 2.23 (s, 3H), 2.69-2.87 (m, 2H), 3.36-3.40 (m, 1H), 6.43 (d, 1H, J=8.0 Hz), 6.80 (d, 2H, J=8.0 Hz); ¹³C-NMR (125 MHz, CDCl₃): δ 20.66, 22.83, 26.83, 30.59, 47.57, 114.53, 121.51, 126.55, 127.46, 130.07, 142.64; Mass spectrum (ESI): 162.15 [M+H]⁺; 92% ee; HPLC (OJ-H, elute: Hexanes/i-PrOH=90/10, detector: 254 nm, flow rate: 0.5 mL/min), (S) t₁=24.2 min, (R) t₂=29.8 min.

6-Methoxy-2-methyl-1,2,3,4-tetrahydroquinoline

¹H-NMR (500 MHz, CDCl₃): δ 1.13 (d, 3H, J=6.0 Hz), 1.46-1.54 (m, 1H), 1.82-1.87 (m, 1H), 2.61-2.66 (m, 1H), 2.73-2.80 (m, 1H), 3.24-3.28 (m, 1H), 3.65 (s, 3H), 6.39 (d, 1H, J=8.5 Hz), 6.51 (t, 2H, J=8.5 Hz); ¹³C-NMR (125 MHz, CDCl₃): δ 22.74, 27.13, 30.51, 47.76, 56.04, 113.09, 114.87, 115.67, 122.87, 138.97, 152.17; Mass spectrum (ESI): 178.13 [M+H]⁺; 94% ee; HPLC (OJ-H, elute: Hexanes/i-PrOH=90/10, detector: 254 nm, flow rate: 0.5 mL/min), (S) t₁=35.2 min, (R) t₂=42.7 min.

2-Phenethyl-1,2,3,4-tetrahydroquinoline

¹H-NMR (500 MHz, CDCl₃): δ 1.71-1.79 (m, 1H), 1.86-1.96 (m, 2H), 2.05-2.08 (m, 1H), 2.79-2.92 (m, 4H), 3.34-3.39 (m, 1H), 3.77 (bs, 1H), 6.53 (d, 1H, J=8.5 Hz), 6.69 (t, 1H, J=7.5 Hz), 7.04 (t, 2H, J=8.0 Hz), 7.28 (t, 3H, J=6.5 Hz), 7.38 (t, 2H, J=6.5 Hz); ¹³C-NMR (125 MHz, CDCl₃): δ 26.51, 28.25, 32.47, 38.50, 51.46, 114.54, 117.44, 121.66, 126.28, 127.05, 128.67, 128.80, 128.86, 129.56, 142.15, 144.72; Mass spectrum (ESI): 237.99 [M+H]⁺; 90% ee;

HPLC (OJ, elute: Hexanes/i-PrOH=90/10, detector: 254 nm, flow rate: 1.0 mL/min), (S) t₁=18.8 min, (R) t₂=20.5 min.

1-(1,2,3,4-tetrahydroquinolin-2-ylmethyl)-cyclohexanol

¹H-NMR (500 MHz, CDCl₃): δ 1.23-1.27 (m, 1H), 1.38-1.68 (m, 13H), 1.74-1.79 (m, 1H), 2.63-2.68 (m, 1H), 2.76-2.83 (m, 1H), 3.48-3.53 (m, 1H), 6.42 (d, 1H, J=7.5 Hz), 6.52 (t, 1H, J=8.5 Hz), 6.87 (t, 2H, J=8.5 Hz); ¹³C-NMR (125 MHz, CDCl₃): δ 22.39, 22.45, 25.97, 26.83, 30.11, 36.00, 40.83, 47.40, 48.11, 72.81, 114.80, 117.07, 121.29, 126.93, 129.47, 144.65; Mass spectrum (ESI): 246.07 [M+H]⁺; 96% ee; HPLC (OJ, elute: Hexanes/i-PrOH=85/15, detector: 254 nm, flow rate: 1.0 mL/min), (S) t₁=7.9 min, (R) t₂=5.1 min.

6-Fluoro-2-methyl-1,2,3,4-tetrahydroquinoline

¹H-NMR (500 MHz, CDCl₃): δ 1.21 (d, 3H, J=6.0 Hz), 1.53-1.61 (m, 1H), 1.90-1.95 (m, 1H), 2.68-2.75 (m, 1H), 2.79-2.88 (m, 1H), 3.29-3.49 (m, 1H), 6.37-6.42 (m, 1H), 6.64-6.70 (m, 2H); ¹³C-NMR (125 MHz, CDCl₃): δ 22.71, 26.94, 30.11, 47.54, 113.30, 113.47, 114.94, 115.00, 115.53, 115.70, 122.73, 141.18, 154.81, 156.67; Mass spectrum (ESI): 165.90 [M+H]⁺; 90% ee; HPLC (OD-H, elute: Hexanes/i-PrOH=94/6, detector: 254 nm, flow rate: 1.0 mL/min), (S) t₁=5.2 min, (R) t₂=6.4 min.

2-Methyl-1-(1,2,3,4-tetrahydroquinolin-2-yl)-propan-2-ol

¹H-NMR (500 MHz, CDCl₃): δ 1.25 (d, 7H, J=5.5 Hz), 1.50-1.69 (m, 3H), 1.75-1.80 (m, 1H), 2.63-2.68 (m, 2H), 2.77-2.84 (m, 1H), 3.48-3.52 (m, 1H), 6.43 (d, 1H, J=8.0 Hz), 6.53 (t, 1H, J=7.5 Hz), 6.88 (t, 2H, J=7.5 Hz); ¹³C-NMR (125 MHz, CDCl₃): δ 26.78, 28.04, 29.96, 33.02, 48.56, 49.12, 72.20, 114.85, 117.15, 121.33, 126.96, 129.51, 144.62; Mass spectrum (ESI): 205.84 [M+H]⁺; 95% ee; HPLC (OD-H, elute: Hexanes/i-PrOH=94/6, detector: 254 nm, flow rate: 1.0 mL/min), (S) $t_1$=9.0 min, (R) $t_2$=11.1 min.

1,2,3,4-Tetrahydro-2-methylquinolin-8-ol $^1$H-NMR (500 MHz, DMSO): δ 1.20 (d, 3H, J=6.5 Hz), 1.43-1.52 (m, 1H), 1.86-1.89 (m, 1H), 2.62-2.67 (m, 1H), 2.73-2.79 (m, 1H), 3.29-3.35 (m, 1H), 4.48 (s, 1H), 6.33 (t, 1H, J=7.5 Hz), 6.42 (d, 1H, J=7.5 Hz), 6.51 (d, 1H, J=7.5 Hz), 9.04 (s, 1H); $^{13}$C-NMR (125 MHz, DMSO): δ 22.99, 26.59, 30.53, 46.81, 112.14, 115.76, 120.40, 120.95, 134.39, 143.80; Mass spectrum (ESI): 164.05 [M+H]$^+$; 97% ee; HPLC (OJ-H, elute: Hexanes/i-PrOH=90/10, detector: 254 nm, flow rate: 1.0 mL/min), (S) $t_1$=22.33 min, (R) $t_2$=24.69 min.

Further in accordance to the present invention, the compounds of formula I-IV are suitable for application to a mammal, such as a human, for the treatment of cancer including solid tumors and non-solid tumors. Notably, the compounds of the present invention are suitable for treatment of breast carcinoma, hepatocellular carcinoma, and chronic myelogenous leukemia. The compounds can be applied in a pharmaceutically acceptable carrier, such as distilled water, deionized water, pharmaceutically acceptable saline water, glucose, dimethyl sulfoxide, and the like.

Effective amount of the applied compound can be from 8 mg/kg/day to about 12 mg/kg/day body weight of the mammal, preferably over a continuous period such as from 5 to 10 days. Application can be by intratumorally injection, intravenous injection, orally, via mucous membrane, inhalation, ingestion, etc. Regarding types of cancer, it is believed the compounds are effective treatment against a wide range of cancer cells, for example, but not limited to Hs578+ and T97D breast cancer cells, K562 cells, and Hep3B cells.

EXAMPLES

Example 1

Synthesis of 8-hydroxy-2-quinolinecarboxaldehyde 8-hydroxy-2-methylquinoline (2 g, 12.4 mmol.), selenium dioxide (1.74 g, 15.8 mmol), 300 ml of pre-dried 1,4-dioxane, and 1.5 ml of water were mixed and stirred in a 1-L round bottom flask. The resulting solution was then refluxed for 24 h. The reaction was monitored until completion using TLC method. The reaction mixture was then filtered off, and the selenium metal was then washed with dichloromethane, and the combined filtrates were then evaporated off under reduced pressure. The crude product was then purified by sublimation under reduced pressure or by silica gel column chromatography to yield pure yellow needle crystal.

Example 2

Synthesis of Compound (Formula I)

To a solution of quinaldine (5 mmol., 716 mg) in 15 mL ether was added a 1.6M solution of n-butyllithium in hexane (5.5 mmol., 3.5 mL) at 0° C. over 30 minutes. This solution was allowed to warm to room temperature and stirred for 1 h.

To the above mixture, a solution of either ketone (5 mmol) in 15 mL ether was added dropwise over 15 minutes with vigorous stirring while the temperature cooled to 0° C. The mixture was then stirred overnight and hydrolysed with a saturated aqueous ammonium chloride solution. The organic layer was separated and the aqueous layer was further extracted with ether (3×50 mL). The combined organic layers were washed with brine and dried over anhydrous sodium sulfate. The solvent was removed under reduced pressure and the crude product was purified by silica gel column chromatography to give the oil product.

Example 3

Synthesis of acetic acid quinolin-2-ylmethyl ether

To a stirred solution of 2-quinolinecarboxaldehyde in methanol was added in portion NaBH$_4$ at room temperature. The reaction was monitored by TLC. After the reaction was completed, the solvent was removed under reduced pressure, and the residue was poured into water, and extracted with dichloromethane (3×10 mL). The combined organic layers were washed with brine, and dried over anhydrous sodium sulphate. The solvent was removed under reduced pressure, and the crude product was purified by silica gel column chromatography to give the alcohol product as colorless oil in quantitative yield.

To a stirred solution of alcohol, acetic anhydride and triethylamine were added. The resulting mixture was stirred at room temperature for 24 hours. The reaction was quenched by adding water, and the mixture was extracted with brine, and dried over anhydrous sodium sulphate. After removal of the solvent, the crude product was subject to silica gel chromatography to give the product in 96% yield.

Example 4

Synthesis of 8-alkoxy-substituted quinaldine

To a solution of 2-methyl-8-quinolinol (3 mmol, 477 mg), alkyl halide (RX, 3 mmol, where X=Br⁻ or Cl) and $K_2CO_3$ were stirred in 10 mL DMF. The reaction was run at room temperature and monitor by TLC. After the reaction was complete, the mixture was washed with $Na_2CO_3$ and extracted with chloroform and then dried over anhydrous sodium sulfate. The solvent was removed under reduced pressure and the crude product was purified by silica gel column chromatography to give the pure product.

Example 5

Synthesis of Compound (Formula II)

1. Ligand can be chiral or non-chiral
2. Ligand can be P-Phos and its derivatives or other phosphine ligands or any possible types of ligand A mixture of [Ir(COD)Cl]$_2$ (1.0 mg, 0.0015 mmol) and the ligand (0.003 mmol) in dried solvent (1.0 mL) was stirred at room temperature for 30 minutes in a glovebox. The mixture was then transferred by a syringe to stainless steel autoclave, in which 12 (4 mg, 0.015 mmol) and substrate (0.3 mmol) in 0.5 mL dried solvent were placed beforehand. The hydrogenation was performed at room temperature under $H_2$ for 20 h. After carefully releasing the hydrogen, the reaction mixture was quenched with saturated sodium carbonate solution (2.0 mL) for 15 minutes. The aqueous layer was extracted with EtOAc (3×3 mL). The combined organic layer was dried with sodium sulfate and concentrated in vacuo to give the crude product. Purification by a silica gel column eluted with hexane/EtOAc gave the heterocyclic compound in pure state. The enantiomeric excesses (ee) were determined by chiral HPLC with chiral column (OJ-H, OD-H or OJ).

Example 6

In Vitro Cytotoxicity Activity Tests

Human breast carcinoma cell line T47D and chronic myelogenous leukaemia (CML) K562 were used for purpose of preliminary anti-cancer screening for the selected alkaloids. Cancer cells (1×10⁴ per well) seeded in the 96 wells microtitre plates for 24 hours were prepared for the alkaloid screening. Compounds a to g (FIG. 1) were prepared as a stock concentration of 50 mg/ml in dimethylsulfoxide (DMSO) and were added at a concentration of 50 µg/ml and incubated for a further of 48 hours. Untreated control received either total complete medium or 0.1% of DMSO. Cisplatinum (CDDP, also at 50 µg/ml) was the positive reference. Afterwards, the evaluation of possible antiproliferative or cytotoxicity of those alkaloids were examined by the One Step ATP lite assay purchased from PerkinElmer according to the technical manual provided. In each experiment, triplicate tests were performed and three independent experiments had been done. Results are shown as mean±standard derivation (SD) of the ATP content when compared with untreated control. Table 2 shows cytotoxicity assay for the tested alkaloid related compounds. Cisplatinum (CDDP) is used as a positive reference. All the testing compounds and CDDP are at a concentration of 50 µg/ml. Results are shown as mean±SD from triplicate experiments.

Figure 1A:
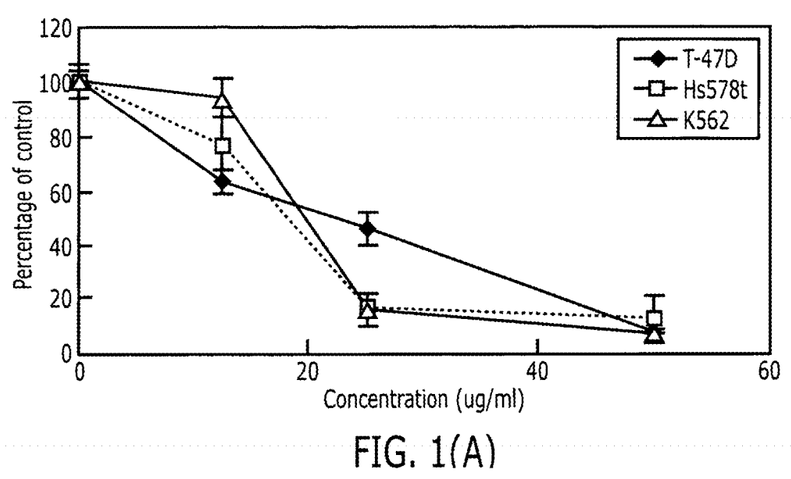
FIG. 1 shows a dose response activity of the present invention on three human cancer cell lines.
Figure 1B:
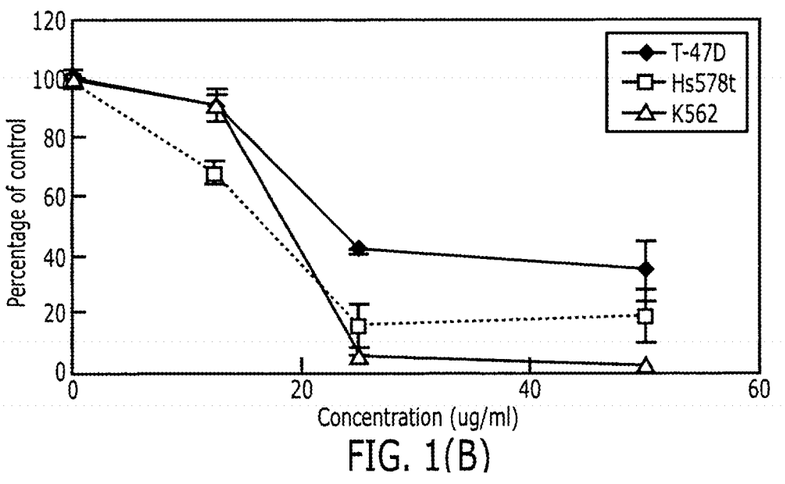
Figure 2A:
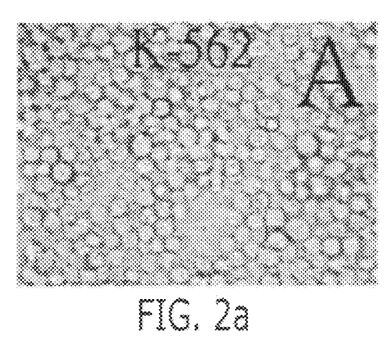
FIG. 2 shows cell shrinkage for breast carcinoma cell lines using the quinoline derivative compounds of the present invention.
Figure 2B:
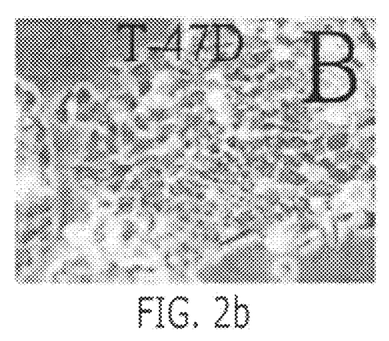
Figure 2C:
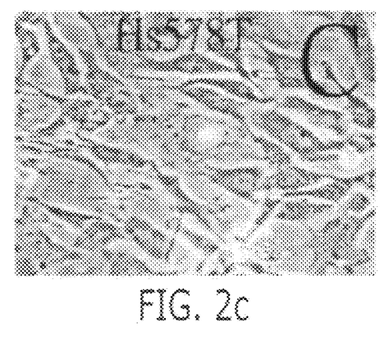
Figure 2D:
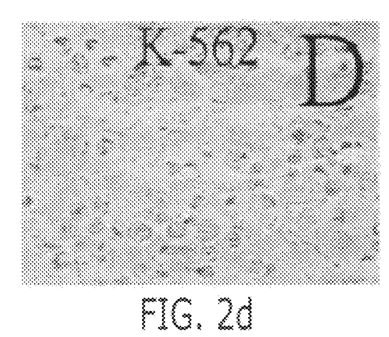
Figure 2E:
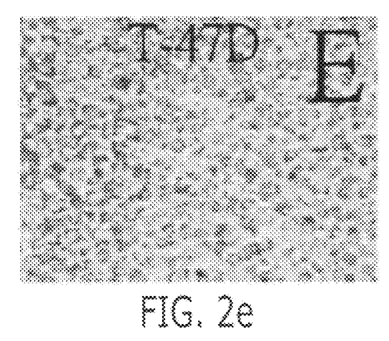
Figure 2F:
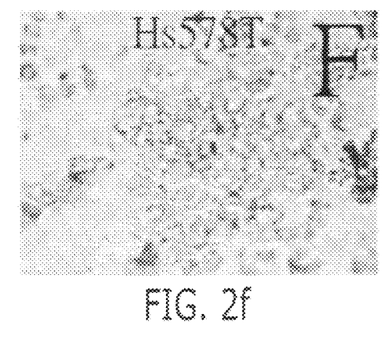

FIG. 1 shows a dose response activity of compound c on three human cancer cell lines including breast carcinoma T47D, Hs578t and CML K562 were further demonstrated. Again, CDDP was used as a positive reference.

TABLE 1

| | |
|---|---|
| a, | $R^1 = CH_3$ and $R^2 = OH$; |
| b, | $R^1 = CH_3$ and $R^2 = OCH_3$; |
| c, | $R^1 = CHO$ and $R^2 = OH$; |
| d, | $R^1 = CN$ and $R^2 = OH$; |
| e, | $R^1 = H$ and $R^2 = OH$; |
| f, | $R^1 = CH_3$ and $R^2 = OCH_2CH_3$; |
| g, | $R^1 = CH_3$ and $R^2 = OCH_2CH_2$-(1-piperidine) |

TABLE 2

| | T-47D | K562 |
|---|---|---|
| Control | 100 ± 6.49 | 100 ± 5.96 |
| DMSO | 109.64 ± 6.73 | 93.39 ± 9.59 |
| a | 46.54 ± 9.40 | 34.46 ± 5.67 |
| b | 37.92 ± 3.57 | 27.15 ± 2.46 |
| c | 8.37 ± 3.46 | 7.00 ± 1.95 |
| d | 72.92 ± 12.01 | 23.08 ± 1.00 |
| e | 52.60 ± 2.36 | 26.66 ± 6.28 |
| f | 63.43 ± 4.81 | 21.38 ± 3.79 |
| g | 69.20 ± 13.36 | 27.43 ± 2.84 |
| CDDP | 30.50 ± 4.83 | 4.17 ± 1.10 |

Example 7

In Vitro Morphological Study for the Cytotoxic Action of Compound c on Cancer Cells Human breast carcinoma cell lines Hs578t, T47D and chronic myelogenous leukaemia K562 were used for the purpose of morphological investigation. Cancer cells ($1\times10^5$ per ml) seeded in the culture plates for 24 hours were prepared for the alkaloid screening. Compounds c from Table 1 was added at a concentration of 25 μg/ml and incubated for a further of 48 hours. Untreated control received 0.05% of DMSO. Any morphological changes were recorded under an inverted microscope. As shown in FIG. 2, all the three cancer cell lines showed cell shrinkage where the two breast carcinoma cell lines also lost the adherent property and cell rounding were observed (d, e and f) where normal growth were observed in the DMSO control (a, b and c).

Example 8

In Vitro Colony Formation Assay

Figure 3:
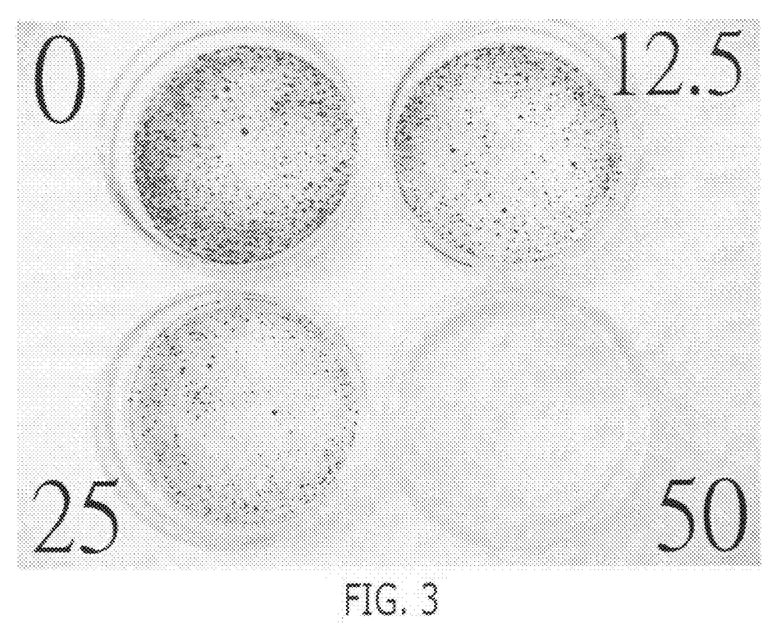
FIG. 3 exhibits a human breast cancer cell line seeded with the present invention.

As shown in FIG. 3, human breast cancer cell line T47D was seeded in the culture disc with a concentration of $1\times10^5$/ml for 24 hours. Afterwards, different concentrations of compound c were added. Untreated control (0) received 0.1% of DMSO. After a further of 24 hours incubation, all the culture medium was removed and fresh complete culture medium was added. The plates were further incubated for 7 days. At last, colonies formed were fixed and stained with methylene blue and photographed. Results here showed that compound c could effectively inhibit the anchorage dependent clonogenicity potential of T47D cells in a dose dependent manner.

Example 9

In Vivo Athymic Nude Mice Xenograft Experiment

Figure 4:
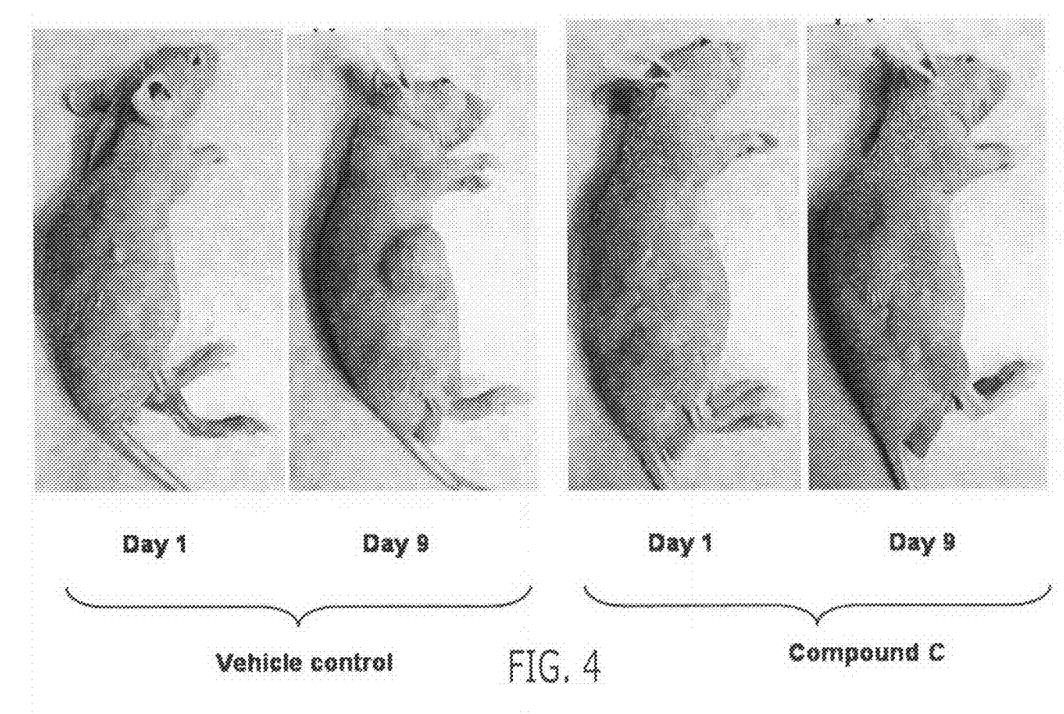
FIG. 4 shows a near complete disappearance of hepatocellular carcinoma in a mouse model.
Figure 5:
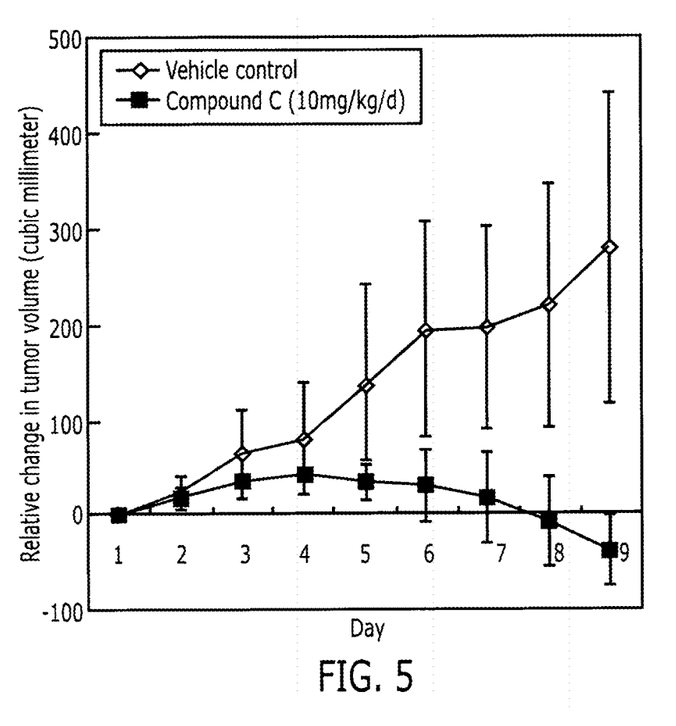
FIG. 5 graphs the disappearance of the carcinoma shown in FIG. 4 based on number of days.

Athymic nude mice purchased from animal house, the Chinese University of Hong Kong with average body weight of 25 g were injected subcutaneously with the human hepatocellular (HCC) cell line Hep3B. They were housed in a sterile condition. Tumor size was measured by the electronic calliper daily. When tumor size reached a mean volume of about 150 mm³ where tumour volume was calculated by the formula (length×width×witdth)/2, they were randomly divided into two groups. Compound c from Table 1 at a concentration of 10 mg/Kg/day body weight was administrated as intraperitoneal injection for a continuous of eight days. Control group received only carrier. Each group consisted of five mice. As shown in the FIGS. 4 and 5, a near complete disappearance of hepatocellular carcinoma Hep3B xenograft was observed in mice received compound c at day nine from the time of drug administration.

Having described embodiments of the present system with reference to the accompanying drawings, it is to be understood that the present system is not limited to the precise embodiments, and that various changes and modifications may be effected therein by one having ordinary skill in the art without departing from the scope or spirit as defined in the appended claims.

In interpreting the appended claims, it should be understood that:
a) the word "comprising" does not exclude the presence of other elements or acts than those listed in the given claim;
b) the word "a" or "an" preceding an element does not exclude the presence of a plurality of such elements;
c) any reference signs in the claims do not limit their scope;
d) any of the disclosed devices or portions thereof may be combined together or separated into further portions unless specifically stated otherwise; and
e) no specific sequence of acts or steps is intended to be required unless specifically indicated.

The invention claimed is:

1. A method of treating cancer in a mammal, the method comprising administering to the mammal an effective amount of a pharmaceutical composition comprising:
(i) a quinoline derivative compound, and
(ii) a pharmaceutically acceptable carrier,
wherein the quinoline derivative compound is selected from the group consisting of 2-ethyl-quinoline, 2-propyl-quinoline, 2-butyl-quinoline, 2-(3-butenyl)-quinoline, 2-pentyl-quinoline, 2-phenethyl-quinoline, 2-methyl-1-(quinolin-2-yl)-propanol, 1,1-diphenyl-2-(quinolin-2-yl)-ethenol, 1-(quinolin-2-ylmethyl)-cyclohexanol, acetic acid quinolin-2-ylmethyl ether, 8-hydroxy-2-quinoline carboxaldehyde, 2-methyl-1,2,3,4-tetrahydroquinoline, 2-ethyl-1,2,3,4-tetrahydroquinoline, 2-propyl-1,2,3,4-tetrahydroquinoline, 2-butyl-1,2,3,4-tetrahydroquinoline, 2,6-dimethyl-1,2,3,4-tetrahydroquinoline, 6-methoxy-2-methyl-1,2,3,4-tetrahydroquinoline, 2-phenethyl-1,2,3,4-tetrahydroquinoline, 1-(1,2,3,4-tetrahydroquinolin-2-ylmethyl)-cyclohexanol, 6-fluoro-2-methyl-1,2,3,4-tetrahydroquinoline, and 2-methyl-1-(1,2,3,4-tetrahydroquinolin-2-yl)-propan-2-ol; and
wherein the cancer is selected from the group consisting of breast carcinoma, hepatocellular carcinoma, and chronic myelogenous leukemia.

2. The method according to claim 1, wherein the cancer is breast carcinoma.

3. The method according to claim 1, wherein the pharmaceutical composition is administered in an amount of from 8 mg/kg/day to about 12 mg/kg/day body weight of the mammal.

4. The method to claim 3, wherein the pharmaceutical composition is administered over a continuous period of between 5 to 10 days.

5. The method according to claim 1, wherein the cancer is hepatocellular carcinoma.

6. The method according to claim 1, wherein the quinoline derivative compound is selected from the group consisting of 8-hydroxy-2-quinoline carbaldehyde, 8-(benzyloxy)-2-methylquinoline, 8-quinolinethiol hydrochloride, and a chiral or a non-chiral tetrahydroquinoline derivative thereof.

7. The method according to claim 6, wherein the chiral or non-chiral tetrahydroquinoline derivative is 1,2,3,4,-tetrahydro-2-methylquinolin-8-ol or 8-(benzyloxy)-1,2,3,4,-tetrahydro-2-methylquinoline.

8. The method according to claim 1, wherein the pharmaceutically acceptable carrier is polyethylene glycol, CMC, or a permanently bonded carrier agent.

9. The method according to claim 1, wherein the pharmaceutically acceptable carrier comprises distilled water, deionized water, glucose, dimethyl sulfoxide or saline water.

10. The method according to claim 1, wherein the mammal is a human.

11. The method according to claim 1, wherein the step of administering comprises intratumorally injection, intravenous injection, oral administration, application via mucous membrane, inhalation, or ingestion.

12. The method according to claim 1, wherein the cancer is chronic myelogenous leukemia.

13. A method of treating cancer in a mammal, the method comprising administering to the mammal an effective amount of a pharmaceutical composition comprising:
(i) a quinoline derivative compound, and
(ii) a pharmaceutically acceptable carrier,
wherein the quinoline derivative compound is selected from the group consisting of 8-hydroxy-2-quinoline carboxaldehyde, 8-hydroxy-2-methylquinoline, 8-methoxy-2-methylquinoline, 8-hydroxy-2-quinoline carbonitrile, 8-hydroxyquinoline, 8-ethoxy-2-methylquinoline, 8-(2-(piperidin-1-yl)ethoxy)-2-methylquinoline, 8-hydroxy-2-quinoline carbaldehyde, 8-(benzyloxy)-2-methylquinoline, 8-quinolinethiol hydrochloride, and 6-methoxy-2-methyl-1,2,3,4-tetrahydroquinoline; and wherein the cancer is selected from the group consisting of breast carcinoma, hepatocellular carcinoma, and chronic myelogenous leukemia.

14. The method according to claim 13, wherein the cancer is breast carcinoma.

15. The method according to claim 13, wherein the pharmaceutical composition is administered in an amount of from 8 mg/kg/day to about 12 mg/kg/day body weight of the mammal.

16. The method according to claim 13, wherein the pharmaceutical composition is administered over a continuous period of between 5 to 10 days.

17. The method according to claim 13, wherein the cancer is hepatocellular carcinoma or chronic myelogenous leukemia.

18. The method according to claim 13, wherein the pharmaceutically acceptable carrier is polyethylene glycol, CMC, or a permanently bonded carrier agent.

19. The method according to claim 13, wherein the pharmaceutically acceptable carrier comprises distilled water, deionized water, glucose, dimethyl sulfoxide or saline water.

20. The method according to claim 13, wherein the mammal is a human.

* * * * *